United States Patent
Zou et al.

(10) Patent No.: US 8,479,592 B2
(45) Date of Patent: Jul. 9, 2013

(54) FIELD STRENGTH TEST DEVICES AND METHODS FOR INSTALLED ENGINEERED MATERIAL ARRESTING SYSTEMS

(75) Inventors: Hong Zou, Chadds Ford, PA (US); Andrea L. Manning, Springfield, PA (US); Graham Kent Thompson, Media, PA (US); Yijian Shi, Swedesboro, NJ (US)

(73) Assignee: Engineered Arresting Systems Corporation, Aston, PA (US)

( * ) Notice: Subject to any disclaimer, the term of this patent is extended or adjusted under 35 U.S.C. 154(b) by 884 days.

(21) Appl. No.: 12/566,206

(22) Filed: Sep. 24, 2009

(65) Prior Publication Data

US 2010/0071474 A1    Mar. 25, 2010

Related U.S. Application Data

(60) Provisional application No. 61/099,937, filed on Sep. 25, 2008.

(51) Int. Cl.
*G01N 33/38* (2006.01)
*G01N 3/44* (2006.01)
*E01C 5/00* (2006.01)
*E01C 3/00* (2006.01)

(52) U.S. Cl.
USPC ........ 73/803; 73/788; 73/790; 73/83; 404/27; 404/34

(58) Field of Classification Search
None
See application file for complete search history.

(56) References Cited

U.S. PATENT DOCUMENTS

| 2,117,985 A | 5/1938 | Ridenour |
| 5,789,681 A | 8/1998 | Angley et al. |
| 5,885,025 A | 3/1999 | Angley et al. |
| 5,902,068 A * | 5/1999 | Angley et al. .............. 404/34 |
| 6,726,400 B1 * | 4/2004 | Angley et al. .............. 404/27 |

FOREIGN PATENT DOCUMENTS

| JP | 6319376 | 11/1994 |
| WO | WO 9835217 | 8/1998 |

OTHER PUBLICATIONS

International Search Report and Written Opinion in related Application No. PCT/US2009/058167.
Letter dated Nov. 1, 2012 with English translation of Office action in related Mexican Application No. MX/A/2011/003240.
Jesus Padron Paz, Hydraulic penetrometer for measuring the soil penetration resistance, $2^{nd}$ part (2005), Published in Cuba as part of fieldwork at the Universidad de Ciego de Avila (UNICA).

* cited by examiner

*Primary Examiner* — Andre Allen
(74) *Attorney, Agent, or Firm* — Dean W. Russell; Kristin M. Crall; Kilpatrick Townsend & Stockton LLP

(57) ABSTRACT

Embodiments of the present invention provide field test devices and methods for testing the compressive gradient strength of installed vehicle arresting systems, such as those installed on airport runways. Current methods of testing such arresting systems are conducted on sample materials in-house, and these methods are not applicable or useful when tests need to be conducted on currently-installed systems in the field.

12 Claims, 3 Drawing Sheets

FIELD STRENGTH TEST DEVICES AND METHODS FOR INSTALLED ENGINEERED MATERIAL ARRESTING SYSTEMS

This application claims the benefit of U.S. Provisional Application Ser. No. 61/099,937, filed Sep. 25, 2008, titled "Field Strength Test Method for Installed Engineered Material Arresting Systems," the entire contents of which are hereby incorporated by reference.

FIELD OF THE INVENTION

Embodiments of the present invention relate generally to a portable test apparatus and test methods for strength testing of low-strength materials, particularly on installed Engineered Material Arresting Systems, hereinafter referred to as EMAS or compressible vehicle arresting systems. One example of an EMAS is described in, among others, U.S. Pat. No. 5,885,025 entitled Vehicle Arresting Bed Systems.

BACKGROUND OF THE INVENTION

One example of an EMAS system or compressible vehicle arresting system comprises material placed at the end of a runway that will predictably and reliably crush (or otherwise deform) under the weight of an aircraft traveling off the end of the runway. The resistance provided by the low-strength material decelerates the aircraft and brings it to a stop within the confines of the overrun area. An object of the EMAS is to fail in a predictable, specified manner, thereby providing controlled, predictable resistive force as the vehicle deforms the EMAS system. An EMAS is thus generally compressible, deformable, crushable, or otherwise able to be compressed or deformed or crushed upon appropriate impact. EMAS is now part of the U.S. airport design standards and is described in FAA Advisory Circular 150/5220-22A "Engineered Materials Arresting Systems (EMAS) for Aircraft Overruns" dated Sep. 30, 2005. EMAS and Runway Safety Area planning are guided by FAA Orders 5200.8 and 5200.9. Alternatively, an EMAS material or compressible (or deformable) vehicle arresting system may be placed on or in a roadway or pedestrian walkway (or elsewhere), for example, for purposes of decelerating vehicles or objects other than aircraft.

The design and manufacturing of EMAS must meet all specified requirements in FAA Advisory Circular 150/5220-22A. Materials of certain strengths are selected to optimize EMAS performance for a specific fleet mix operating on a specific runway. The lifecycle cost calculations from FAA Order 5200.9 assume that EMAS may require replacement at a certain time. In order to determine that installed EMAS systems have maintained designed vehicle arresting capability, a field strength test device and test method needs to be developed to measure the strength of installed EMAS over time.

U.S. Pat. No. 5,789,681 describes one example of a test apparatus and test method for EMAS material. This patent also defines the Compressive Gradient Strength (CGS) standard, which has been used in-house to control material strength in production. However, this patented in-house test method cannot be directly applied to field strength testing of installed EMAS systems at least because the test apparatus is not portable. This system tests an arresting material test section that is positioned on a bearing block. A load is then applied to the test section (using a hydraulic system that controls a shaft with a test probe head) at a relatively fast constant speed with force measurement occurring continuously or at small increments of displacement as the test probe head moves through the sample. However, if one wishes to test an EMAS system that has already been installed, removing one or more portions of the material from the system and transporting those portions back to the laboratory for testing is impractical and unreliable. Examples of potential problems are that the material may be cracked during removal of the test piece, or the entire system may be compromised from the removal of the testing piece, both causing problems with the testing process. Removal of a test piece in some cases conceivably could require that the entire EMAS bed be placed out of service, potentially precluding use of the associated runway for an extended period.

Embodiments of the invention described herein thus provide a strength test device and method that can be easily implemented in the field, on an existing and currently-installed EMAS (i.e. in situ). The desired portable test apparatus should take readings for resistive load and penetration depth. The measured resistive load can be converted into CGS. The penetration depth in the material can be measured using different types of distance measurement devices.

Although some off-the-shelf soil penetrometers are capable of taking both resistive load and distance measurements, they cannot be directly applied to field strength testing of EMAS materials with their current designs. These penetrometers were designed mostly for soil compaction study. For example, the American Society of Agricultural Engineers (ASAE) and the American Society for Testing and Materials (ASTM) require the use of punch heads with cone shapes, which are particularly designed for soil testing, but they cannot be used for EMAS testing due to the unique properties of EMAS materials. Accordingly, embodiments of this invention provide a portable system and testing method for testing various features of currently-installed EMAS systems.

SUMMARY

There is a great need for field strength testing of installed EMAS systems. However, neither the patented in-house EMAS test apparatus nor the penetrometers for soil testing meet the specialized needs for EMAS field testing. Accordingly, embodiments of this invention provide a field strength test device and method that include hardware design, sample size determination, random sampling, and strength data interpretation. The described strength test devices and methods can be applied not only to existing EMAS systems, but also to new generations of EMAS, which may utilize other low-strength materials having similar arresting capabilities. Each type of material will have a unique tolerance band associated with a selected punch head size. Those tolerance bands will likely be pre-set by a regulatory authority or by an EMAS system manufacturer, and are set at the time of installation. However, the tolerance bands of the installed system should be appropriately tested at various intervals after installation using the devices and methods described herein in order to confirm that the materials are maintaining the desired and required strength over time.

DETAILED DESCRIPTION

Figure 1:
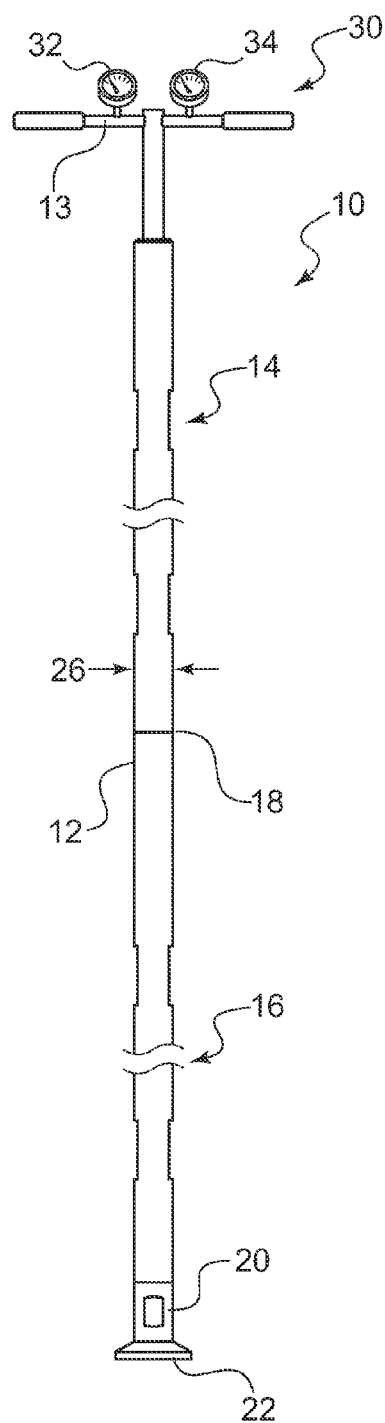
FIG. 1 shows a side plan view of one embodiment of a field testing device.
Figure 2:
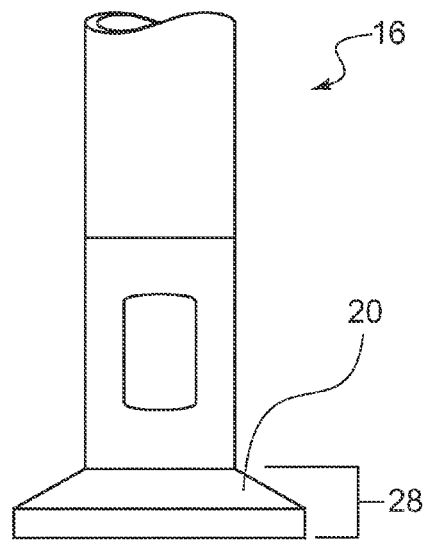
FIG. 2 shows a close-up view of one end of the field testing device of FIG. 1.

As shown in FIG. 1, one embodiment of a portable field testing device 10 includes a shaft 12, a punch head 20, and a measurement system 30. For increased portability, the shaft 12 may (but need not) be divided into two or more sections and assembled on-site. In the specific example shown in FIG. 1, shaft 12 is provided in two parts, an upper shaft 14 and a lower shaft 16, that can be quickly assembled in the field but provide for easy transportation. It should be understood, however, that a single shaft or any number of shaft sections may be provided. As also shown in the specific embodiment of FIG. 1, the upper and lower shaft portions 14, 16, may be connected via a threaded connection 18. Again, it should be understood that any number of appropriate connections may be used and are considered within the scope of this invention, such as snap fit connections, j lock/tab connections, dovetail connections, tapered connections, and so forth.

In a specific embodiment, the punch shaft 12 is at least about 25 inches long in order to cover desired maximum penetration depth. Depending upon the type of materials to be tested, the shaft 12 should generally be at least about 5 inches long, but may be anywhere from 5 to 36 inches, and even longer if that eases use. In general, the length should be optimized for ease of operation to maintain a constant penetration speed.

Figure 3:
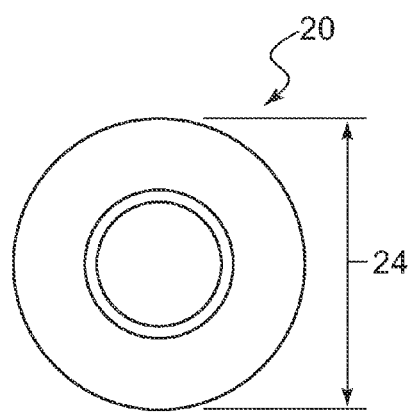
FIG. 3 shows a bottom plan view of one embodiment of a punch head of the field testing device of FIG. 1.

Device 10 also includes a punch head 20 at its lower portion. One type of punch head 20 has a flat lower surface 22 and a generally round diameter 24, as shown in FIG. 3. In one embodiment, the field testing device 10 may be based on a design with capabilities of taking measurements on resistive load and penetration depth. In other embodiments, the field testing device 10 may be built based on an existing soil penetrometer with a modified punch head and shaft.

Figure 4:
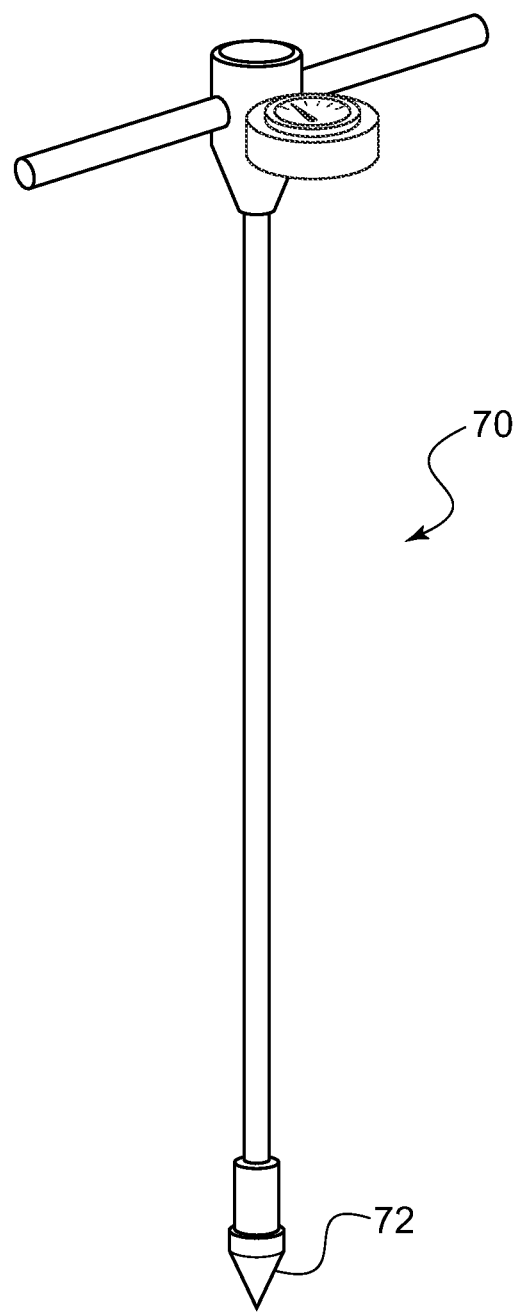
FIG. 4 shows an example of a prior art soil penetrometer prior to being modified according to various embodiments of this invention.
Figure 5:
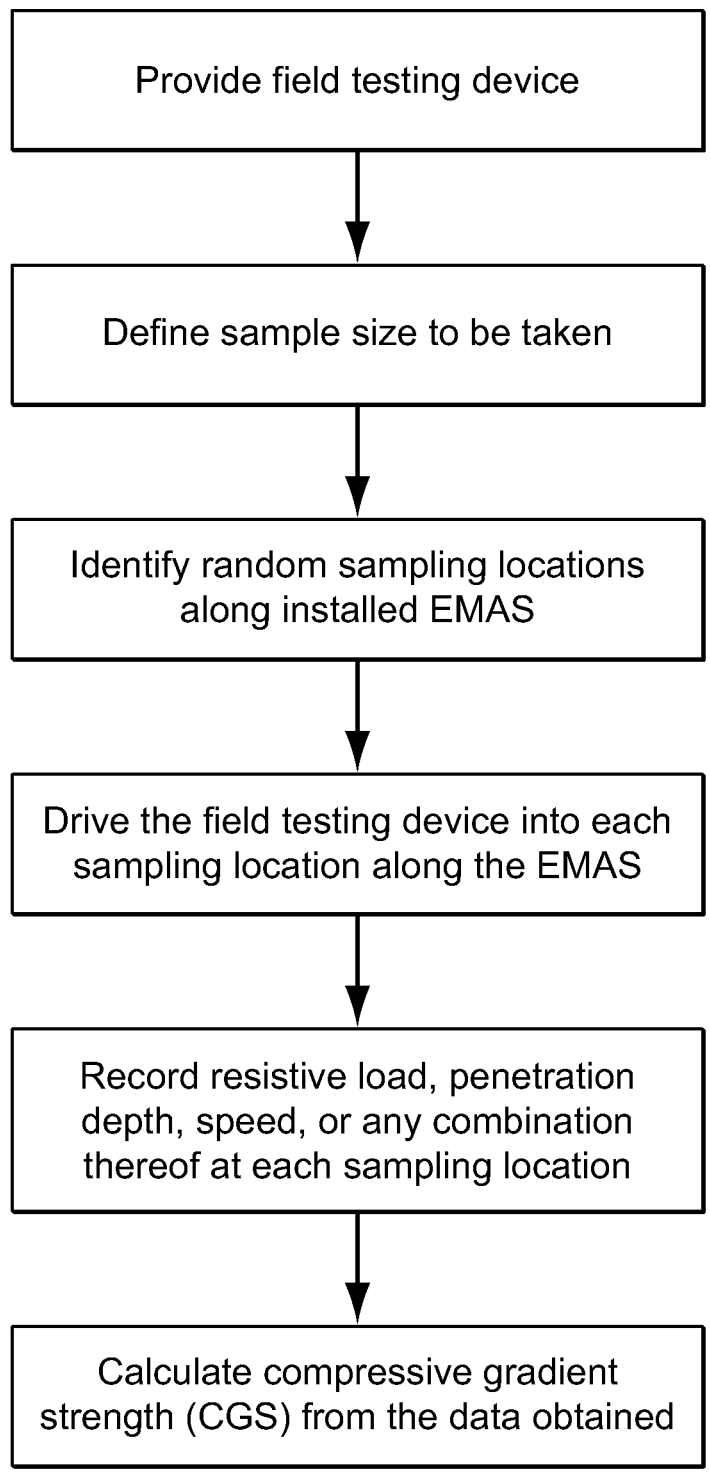
FIG. 5 shows a schematic of testing steps according to one testing method embodiment.

One example of a soil penetrometer 70 is shown in FIG. 4. Although various options for such devices exist, soil penetrometers generally have a cone-shaped or pointed punch head 72 that is designed to penetrate soil in order to measure various parameters. Soil penetrometers generally have a punch head for soil testing with either a 30° or 60° cone shape, as provided for by ASAE and ASTM standards. This is so that the pointed end of the soil penetrometer can penetrate soil easily.

Obviously, such a device would not be useful for testing the compressive gradient strength of an EMAS. The goal for such testing is not necessarily to penetrate the EMAS, but to determine its failure upon a certain applied load across a certain defined area. As such, the field testing device 10 for testing an existing EMAS system has been designed with a punch head 20 preferably having a flat lower surface 22. Punch head 20 is also provided in a generally round or circular shape. The flat circular shape is selected so the punch head 20 overcomes the resistance primarily from the CGS strength of the material. The thickness 28 of the punch head 20 has been designed to minimize the friction resistance from the punch head 20. By contrast, the cone-shaped head of a soil penetrometer would immediately penetrate the EMAS without testing an appropriate resistance at all. The material of the punch head should be chosen to resist wear due to abrasion by EMAS material. Non-limiting examples include any appropriate type of metal, polymer, or ceramic, or any combination or alloy thereof. It should be understood that punch head 20 may have a different effective surface and need not be perfectly flat and round. A suitable head size can be selected for testing certain strength material. Non-limiting examples of possible punch diameters range from about 0.5 to about 2.0 inches, although it should be understood that they may be larger or smaller, depending on the material and circumstances of the testing.

The punch shaft 12 is shown in FIG. 1 as having a diameter 26 that is smaller than the diameter 24 of the punch head 20. This design helps eliminate the friction load from the shaft 12. It is also possible for the punch shaft 12 to be about the same size or equal to the diameter 24 of the punch head 20. The shaft 12 should also be sturdy enough to avoid buckling due to resistive load. The material of the shaft should be selected to resist wear for intensive use, examples of which may be the same as those provided above for the punch head 20.

The device 10 also includes a handle 13 or some other type of gripping or stabilizing element at its upper portion. As shown in FIG. 1, handle 13 may support a measurement system 30 for measuring the desired parameters that are being tested in the field (however, it should be understood that measurement system 30 may be located anywhere along shaft 12 as desired). In one embodiment, the penetration depth of the punch head 20 can be measured using various distance or penetration depth sensors 32, such as ultrasonic and laser sensors. The selection of a distance sensor 32 will depend on required accuracy and environmental ruggedness. Because the material strength is sensitive to deformation rate, it is important to control penetration speed, which will significantly affect the resistive load measurement. The penetration speed can be calculated from penetration depth measurements. A speed indicator 34 can be used to assist in controlling the punch head speed. A resistive load sensor (not shown, but similar to the other sensors indicated on the handle) may also be provided.

Determining a sample size is also important because oversized samples waste time and resources, while a sample size that is too small may be statistically insignificant and lead to inaccurate test results. The sample size can be determined primarily by desired level of precision, confidence level, and degree of variability in material strength. It is also important to use random sampling in order to reliably determine the mean strength of an EMAS system within a desired confidence interval. The location of samples for field strength testing can be determined using ASTM D 3665 on an effective EMAS arrestor area, which can be defined according to the EMAS design and maintenance standards.

One embodiment of a method that may be used for field testing the strength of an installed EMAS system is to provide an appropriate field testing device, define a sample size to be taken, and identify sampling locations along the installed EMAS. The sampling locations (and specifically, random sampling locations) may be identified by a computer program in order to prevent operator error in location decisions. However, it is also possible for the operator to identify random locations along the EMAS, making sure to test at various heights and distances along the EMAS (e.g., not all samples should be located at the base of the EMAS and not all samples should be taken on one side or all on the other side on the EMAS, but along a good sampling of differing heights and distances).

The operator should then drive the field testing device into each sampling location along the EMAS, record the resistive load, penetration depth, punch head speed. or any combination at each sampling location. Once all data has been obtained, the compressive gradient strength (CGS) of the material is calculated from the data obtained. This calculation may be done manually or by an appropriate computer program that receives and runs the data, and provides an output summary of the findings.

Using the test procedure described above, resistive loads at randomly selected locations can be recorded as functions of penetration depth and later be downloaded onto a computer for analysis. The material strength, CGS, can be calculated based on the associated punch head size. Being equivalent or similar to the tolerance bands defined in U.S. Pat. No. 5,789,681 for in-house testing, field test tolerance bands should be developed for materials of certain strength and associated punch heads. The calculated material strength should be compared with a specific field test tolerance band. For example, once the CGS has been identified, it may be compared to defined CGS limits. The resultant material strength should then be presented as a confidence interval based on statistical analysis.

Field strength testing should be conducted regularly to find the trend of strength change over time and to confirm that the installed system is maintaining its required strength. Integrated with other field inspection methods, the field strength test method described in this invention will help monitor the condition of installed EMAS systems.

Changes and modifications, additions and deletions may be made to the structures and methods recited above and shown in the drawings without departing from the scope or spirit of the invention and the following claims.

What is claimed is:

1. A method for field strength testing an installed compressible vehicle arresting system, comprising:
    (a) providing a portable field testing device;
    (b) identifying sampling locations along the installed compressible vehicle arresting system;
    (c) driving the portable field testing device into each sampling location along the system; and
    (d) recording desired parameters at each sampling location.

2. The method of claim 1, wherein the desired parameters comprise resistive load, penetration depth, punch head speed, or any combination thereof.

3. The method of claim 2, further comprising calculating compressive gradient strength (CGS) from the resistive load, penetration depth, punch head speed, or any combination thereof obtained.

4. The method of claim 2, further comprising calculating compressive gradient strength (CGS) from the resistive load, penetration depth, punch head speed, or any combination thereof obtained and comparing that CGS to defined CGS limits.

5. The method of claim 1, wherein the sampling locations identified are random.

6. A portable field testing device for installed compressible vehicle arresting system, comprising:
    (a) a shaft having a length and a diameter;
    (b) a punch head at one end of the shaft having a flat surface;
    (c) a measurement system configured to measure desired parameters; and
    (d) a handle configured to stabilize the portable field testing device in use,
    wherein the shaft is provided in more than one section for portability, and wherein the more than one sections are connectable to one another in use in the field.

7. The method of claim 1, wherein the portable field testing device is the device recited by claim 6.

8. The portable field testing device of claim 6, wherein the measurement system comprises a resistive load sensor, a penetration depth sensor, a speed indicator, or any combination thereof.

9. The portable field testing device of claim 6, wherein the shaft diameter is smaller than or equal to the punch head diameter.

10. The portable field testing device of claim 6, wherein the length of the shaft is from about 5 to about 36 inches.

11. The portable field testing device of claim 6, wherein the desired parameters comprise resistive load, penetration of the punch head into the installed compressible vehicle arresting system, the speed of the punch head into the installed compressible vehicle arresting system, or any combination thereof.

12. The portable field testing device of claim 6, wherein the measurement system is mounted on the handle.

* * * * *